United States Patent [19]
Yanaka et al.

[11] Patent Number: 5,585,381
[45] Date of Patent: Dec. 17, 1996

[54] PYRIMIDINE DERIVATIVES AND PHARMACEUTICAL COMPOSITION

[75] Inventors: Mikiro Yanaka, Chiba; Fuyuhiko Nishijima; Hiroyuki Enari, both of Tokyo; Michihito Ise, Saitama, all of Japan

[73] Assignee: Kureha Chemical Industry Co., Ltd., Tokyo, Japan

[21] Appl. No.: 454,629

[22] Filed: May 31, 1995

[30] Foreign Application Priority Data

Jun. 1, 1994 [JP] Japan .................................. 6-142274

[51] Int. Cl.$^6$ ................ C07D 239/48; A61K 31/505
[52] U.S. Cl. .................. 514/275; 514/256; 514/269; 544/317; 544/319; 544/324; 544/323; 544/328; 544/329; 544/326; 544/327
[58] Field of Search ............... 514/256, 269, 514/275; 544/317, 319, 326, 327, 328, 329, 323, 324

[56] References Cited

FOREIGN PATENT DOCUMENTS 0156559 10/1985 European Pat. Off. .
0561175 9/1993 European Pat. Off. .

OTHER PUBLICATIONS

Melik–Ogandzhanyan et al, "New Method for the Synthesis of Some Polyfunctional 5–Aminopyrimidines", Chemical Abstract No. 179322e, 98(28):655 (1983).
*Khim, Geterozykl, Soedin*, 1:115–118 (1983) (In Russian).
Kelley et al, Chemical Abstracts, vol. 106, entry 67252 (1987).

*Primary Examiner*—John M. Ford
*Attorney, Agent, or Firm*—Sughrue, Mion, Zinn, Macpeak & Seas

[57] ABSTRACT

A pyrimidine derivative of the formula (I):

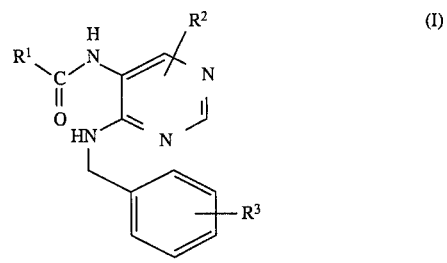

wherein $R^1$ is a hydrogen atom, alkyl of 1 to 6 carbon atoms, haloalkyl of 1 to 6 carbon atoms, or —$NHR^{11}$ group; $R^2$ is a hydrogen or halogen atom, alkyl of 1 to 6 carbon atoms, haloalkyl of 1 to 6 carbon atoms, —$(CH_2)_mC_6H_5$, —$NH_2$, —$NHR^{12}$, —$NH(CH_2)_nC_6H_5$, —$NH(CH_2)_pC_6H_4$—$OR^{13}$, —$N(R^{14})(CH_2)_qC_6H_5$, —$NHC(=O)R^{15}$, —$NHC(=O)(CH_2)_rC_6H_5$, —$NHC(=O)CH(C_6H_5)_2$, —$OR^{16}$, or —$O(CH_2)_sC_6H_5$ group; $R^3$ is —COOH, —$COOR^{17}$, hydroxyl, —$OR^{18}$, —$NH_2$, —$N(R^{19})_2$, —$NHR^{20}$, azole, or sulfonic acid group; $R^{11}$ is alkyl of 1 to 6 carbon atoms or haloalkyl of 1 to 6 carbon atoms; $R^{12}$, $R^{13}$, $R^{14}$, $R^{15}$, $R^{16}$, $R^{17}$, $R^{18}$, $R^{19}$, and $R^{20}$ are independently alkyl of 1 to 6 carbon atoms; m is 0 or an integer of 1 to 6; n is 0 or an integer of 1 to 6; p is 0 or an integer of 1 to 6; q is 0 or an integer of 1 to 6; r is 0 or an integer of 1 to 6; and s is 0 or an integer of 1 to 6, or a salt thereof, and a pharmaceutical composition comprising said pyrimidine derivative or a pharmaceutically acceptable salt thereof, and a pharmaceutically acceptable carrier are disclosed.

7 Claims, No Drawings

PYRIMIDINE DERIVATIVES AND PHARMACEUTICAL COMPOSITION

BACKGROUND OF THE INVENTION

1. Field of the Invention

The present invention relates to a novel pyrimidine derivative or a salt thereof, and a pharmaceutical composition, particularly, an agent for treating a kidney disease, containing said pyrimidine derivative or a pharmaceutically acceptable salt thereof. Although the pyrimidine derivative of the present invention exhibits substantially no or very weak antagonism to the angiotensin II receptor subtype 1 which participates in action to depress blood pressure, it can sufficiently improve a kidney disease.

2. Description of the Related Art

Recently, there is an increasing tendency of patients suffering from renal dysfunction. The reason is believed that a development of drugs appropriate to treat kidney diseases is behind with an increasing aged population or changes in living environment. Therefore, the drugs appropriate to treat kidney diseases have been strongly desired.

More particularly, a method for treating lesions accompanying diseases, i.e., the nosotropic treatment, is mainly used as yet for kidney diseases, such as nephritis, diabetic nephropathy or renal failure. For example, an antihypertensive, diuretic or anti-inflammatory agent, or dietary treatment, kinesitherapy or the like is mainly used. Because kidney diseases are accompanied with hypertension and the hypertension is believed to be one of factors aggravating kidney diseases, the antihypertensive agents are often used. Of the antihypertensive agents, the agents to inhibit production or function of angiotensin II are attempted in many cases. This is because that angiotensin II is believed to be a factor aggravating kidney diseases due to its activities to raise blood pressure and accelerate growth of interstitial cells in the kidney, and elimination of such a factor as much as possible is believed to improve the kidney diseases.

It is reported in J. Clin. Pharmacol., 30:155–158, 1990 that when the antihypertensive agent (such as enalapril or captoril), namely, the agent to inhibit the enzyme to convert angiotensin I to angiotensin II which exhibits the activity to raise blood pressure (angiotensin converting enzyme; ACE), i,e., the angiotensin converting enzyme inhibitor (ACEI), is used, blood pressure is lowered and the progress of renal dysfunction is improved. U.S. Pat. No. 5,071,867 suggests that because the improvement of the renal dysfunction is observed in rats suffering therefrom by administering the antihypertensive agent in an amount larger than that usually used to lower blood pressure, human will become endurable to a large dose if the dose is carefully and gradually increased, and to thereby enjoy the benefit of curing the renal dysfunction in human. On the other hand, it is pointed out in "Saishin Igaku (Latest Medicine)", 48: 1404–1409, 1993 that such agents have side effects such as dry-cough as their inherent properties, or are attended with danger to lower blood pressure and then cause acute renal failure, and therefore should be carefully administered.

Thereafter, an angiotensin II receptor antagonist (AGI-IRA) was developed as a antihypertensive agent. Two kinds of the angiotensin II receptors, the subtype 1 and the subtype 2, are known at the present. Although the functions of the subtype 2 are not sufficiently elucidated, the subtype 1 is known to participate in blood pressure. Therefore, the subtype 1 receptor antagonist is a target of the development of the antihypertensive agent.

As the compounds which are antihypertensive agents exhibiting a strong antagonizing activity to the angiotensin II receptor, and at the same time, are examined for their action to kidney diseases, the imidazole derivative, 2-butyl-4-chloro- 5-(hydroxymethyl)-1-[[2'-(1H-tetrazol- 5-yl )biphenyl-4 -yl]methyl]imidazole (Dup753 or MK954) is known. When the imidazole derivative was administered to renal dysfunction model rats, it was effective against proteinuria and glomerulosclerosis, but at the same time the reduction of blood pressure accompanied (J. Clinical Invest., 90: 766–771, 1992). Further, when the above imidazole derivative was administered to hyperlipemia model rats, the kidney disease was improved in a lower dose without practical effect to blood pressure, but an evident reduction of blood pressure was observed at a large dose more effective against the kidney disease (Nephron, 65: 426–432, 1993).

Further, compounds having the structures similar to that of the above imidazole derivative are disclosed in Japanese Unexamined Patent Publication No. 63-23868, and U.S. Pat. No. 5,153,197, U.S. Pat. No. 5,128,355 and U.S. Pat. No. 5,155,118. Japanese Unexamined Patent Publication No. 63-23868 discloses that such compounds are effective against hypertension and congestive heart failure. U.S. Pat. No. 5,153,197 discloses that such compounds are effective against hypertension. U.S. Pat. No. 5,128,355 discloses that such compounds are effective against heart failure. U.S. Pat. No. 5,155,118 discloses that such compounds are effective against renal failure caused by non-steroid anti-inflammatory agent. However, all the imidazole derivatives disclosed in said Japanese Unexamined Patent Publication and U.S. Patents are characterized by a strong angiotensin II receptor antagonism, and have an activity to lower blood pressure.

EP 0475206A2 discloses the compounds having a pyrimidine skeleton and its application to kidney diseases. However, the pyrimidine compounds are characterized by a strong angiotensin II receptor antagonism accompanied by the lowering function of blood pressure. Further, it is reported in J. Pharmacol. Experimental Therapeutics, 267: 657–663, 1993 that when one of the pyrimidine analogues, 2-[N-propyl-N-[[2'-(1H-tetrazol-5-yl)biphenyl-4-yl]methyl] amino]pyridine-3-carboxylic acid (A-81988), was administered to kidney disease model rats, proteinuria was improved, but at the same time, the reduction of blood pressure was observed. The above pyrimidine analogues exhibits the function to lower blood pressure due to the strong angiotensin II receptor antagonism, and therefore, there is a fear of acute renal failure or the like when administered to the person suffering from kidney diseases.

As above, hitherto, drugs having the function to strongly lower blood pressure were basically desired in the treatment of the kidney diseases by the antihypertensive agent. In the kidney disease, the hypertension is an important symptom to be improved. However, mere lowering of blood pressure is not favorable. It is important to maintain appropriate blood pressure. Thus, it is necessary to adjust blood pressure by combining the kinds and the doses of the antihypertensive agents in view of the symptom. However, continuous treatment with a sufficient dose is desired for the kidney diseases per se. Therefore, so long as a conventional antihypertensive agent is used, it is fundamentally impossible to appropriately adjust blood pressure and at the same time to effectively cure the kidney disease by the sole antihypertensive agent. One of such problems is, for example, the above acute renal failure caused by the antihypertensive agent used.

SUMMARY OF THE INVENTION

The inventors of the present invention engaged in intensive studies to find the compounds having the properties which were completely unknown in the past, namely the compounds sufficiently effective in improvement of the renal dysfunction without any function to blood pressure, and as a result, found novel pyrimidine derivatives which are sufficiently effective in improvement of the renal dysfunction while the antagonism thereof to the angiotensin II receptor subtype 1 is one-hundredth ($\frac{1}{100}$) to one-thousandth ($\frac{1}{1000}$) or less as large as that of the conventional antagonist having a standard activity as a antihypertensive agent. The present invention is based on the finding.

Accordingly, the present invention relates to a pyrimidine derivative of the formula (I):

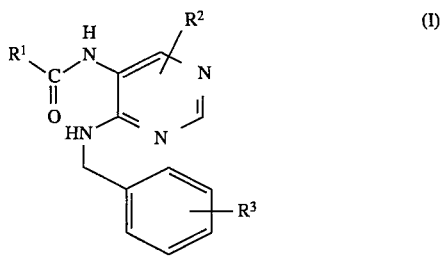

wherein $R^1$ is a hydrogen atom, alkyl of 1 to 6 carbon atoms, haloalkyl of 1 to 6 carbon atoms, or —$NHR^{11}$ group; $R^2$ is a hydrogen or halogen atom, alkyl of 1 to 6 carbon atoms, haloalkyl of 1 to 6 carbon atoms, —$(CH_2)_mC_6H_5$, —$NH_2$, —$NHR^{12}$, —$NH(CH_2)_nC_6H_5$, —$NH(CH_2)_pC_6H_4$—$OR^{13}$, —$N(R^{14})(CH_2)_qC_6H_5$, —$NHC(=O)R^{15}$, —$NHC(=O)(CH_2)_rC_6H_5$, —$NHC(=O)CH(C_6H_5)_2$, —$OR^{16}$, or —$O(CH_2)_sC_6H_5$ group; $R^3$ is —COOH, —$COOR^{17}$, hydroxyl, —$OR^{18}$, —$NH_2$, —$N(R^{19})_2$, —$NHR^{20}$, azole, or sulfonic acid group; $R^{11}$ is alkyl of 1 to 6 carbon atoms or haloalkyl of 1 to 6 carbon atoms; $R^{12}$, $R^{13}$, $R^{14}$, $R^{15}$, $R^{16}$, $R^{17}$, $R^{18}$, $R^{19}$, and $R^{20}$ are independently alkyl of 1 to 6 carbon atoms; m is 0 or an integer of 1 to 6; n is 0 or an integer of 1 to 6; p is 0 or an integer of 1 to 6; q is 0 or an integer of 1 to 6; r is 0 or an integer of 1 to 6; and s is 0 or an integer of 1 to 6, or a salt thereof.

Further, the present invention relates to a pharmaceutical composition comprising a pyrimidine derivative of the formula (I) or a pharmaceutically acceptable salt thereof and a pharmaceutically acceptable carrier or diluent.

DETAILED DESCRIPTION OF THE PREFERRED EMBODIMENTS

The term "alkyl" as used herein includes straight-chain and branched alkyl groups, for example, an alkyl group of 1 to 4 carbon atoms, such as methyl, ethyl, n-propyl, i-propyl, n-butyl, i-butyl, s-butyl or t-butyl; an alkyl group of 1 to 5 carbon atoms, such as those as mentioned above, n-pentyl, i-pentyl, neopentyl, t-pentyl, 1-methylbutyl, 2-methylbutyl, 1,2-dimethylpropyl or 1-ethylpropyl; and an alkyl group of 1 to 6 carbon atoms, such as those as mentioned above, n-hexyl, i-hexyl or 2-ethylbutyl.

The halogen atom is, for example, a chlorine, bromine, fluorine or iodine atom. The haloalkyl group of 1 to 6 carbon atoms is the above alkyl group of 1 to 6 carbon atoms substituted with 1 to 13 halogen atoms as mentioned above. The preferred haloalkyl group is, for example, a trifluoromethyl, pentafluoroethyl, or 4,4,4-trifluorobutyl.

The azole group is a 5-membered cyclic group containing 2 to 4 heteroatoms, such as a nitrogen, oxygen or sulfur atom, such as a group of imidazole, oxazole, thiazole, pyrazole, isoxazole, isothiazole, triazole, oxadiazole, thiadiazole, tetrazole, oxatriazole or thiatriazole. The preferred azole group is a tetrazole group.

The compound of the formula (I) wherein $R^1$ is a hydrogen atom, alkyl of 1 to 5 carbon atoms, haloalkyl of 1 to 5 carbon atoms, or —$NHR^{11}$ group; $R^2$ is a hydrogen or halogen atom, alkyl of 1 to 4 carbon atoms, haloalkyl of 1 to 4 carbon atoms, —$(CH_2)_mC_6H_5$, —$NH_2$, —$NHR^{12}$, —$NH(CH_2)_nC_6H_5$, —$NH(CH_2)_pC_6H_4$—$OR^{13}$, —$N(R^{14})(CH_2)_qC_6H_5$, —$NHC(=O)R^{15}$, —$NHC(=O)(CH_2)_rC_6H_5$, —$NHC(=O)CH(C_6H_5)_2$, —$OR^{16}$, or —$O(CH_2)_sC_6H_5$ group; $R^3$ is —COOH, —$COOR^{17}$, hydroxyl, —$OR^{18}$, —$NH_2$, —$N(R^{19})_2$, —$NHR^{20}$, azole group, or sulfonic acid group; $R^{11}$ is alkyl of 1 to 5 carbon atoms or haloalkyl of 1 to 5 carbon atoms; $R^{12}$, $R^{13}$, $R^{14}$, $R^{15}$, $R^{16}$, $R^{17}$, $R^{18}$, $R^{19}$, and $R^{20}$ are independently alkyl of 1 to 4 carbon atoms; m is 0 or an integer of 1 to 4; n is 0 or an integer of 1 to 4; p is 0 or an integer of 1 to 4; q is 0 or an integer of 1 to 4; r is 0 or an integer of 1 to 4; and s is 0 or an integer of 1 to 4, or a salt thereof is preferable.

The compound of the formula (I) wherein $R^2$ is at 2- or 6-position of the pyrimidine ring, and $R^3$ is at 4-position of the phenyl ring, or a salt thereof is more preferable.

The compound of the formula (I) wherein $R^2$ is at 6-position of the pyrimidine ring, and $R^3$ is at 4-position of the phenyl ring, or a salt thereof is most preferable.

The salt of the compound of the present invention includes a salt with an inorganic or organic acid or a salt with an inorganic or organic base, preferably a pharmaceutically acceptable salt. As an acid additive salt, there may be mentioned, for example, hydrochloride, sulfate, methanesulfonate or p-toluenesulfonate; a salt with a dicarboxylic acid, such as oxalic, malonic, succinic, maleic or fumaric acid; or a salt with a monocarboxylic acid, such as acetic, propionic or butyric acid. The inorganic base suitable to form a salt of the compound of the present invention is, for example, a hydroxide, carbonate or bicarbonate of ammonium, sodium, lithium, calcium, magnesium or aluminum. As the salt with the organic base, there may be mentioned, for example, a salt with a mono-, di- or tri-alkylamine, such as methylamine, dimethylamine or triethylamine; a salt with a mono-, di- or tri-hydroxyalkylamine, guanidine, N-methylglucosamine or amino acid salt.

As the typical examples of the compounds according to the present invention, the structures of Compounds No. 1 to 90 are shown in the following Tables 1 to 3. Further, the results of elemental and mass spectrometric analyses are listed in Tables 4 to 6. The compounds listed in the following Tables are sometimes referred to the numbers in the following Tables. In the following Tables, Me is methyl, Et is ethyl, Pr is propyl, Bu is butyl, Pen is pentyl, Hex is hexyl and Ph is phenyl.

TABLE 1

| No. | $R^1$ | $R^2$ | $R^3$ | Molecular formula |
|---|---|---|---|---|
| 1 | n-Bu | 6-Cl | 4-COOMe | $C_{18}H_{21}N_4O_3Cl$ |
| 2 | n-Bu | 6-OMe | 4-COOH | $C_{18}H_{22}N_4O_4$ |
| 3 | n-Bu | 6-NHCH$_2$Ph | 4-COOMe | $C_{25}H_{29}N_5O_3$ |
| 4 | n-Bu | 6-NH(CH$_2$)$_2$Ph | 4-COOMe | $C_{26}H_{31}N_5O_3$ |
| 5 | n-Bu | 6-NH(CH$_2$)$_3$Ph | 4-COOMe | $C_{27}H_{33}N_5O_3$ |
| 6 | n-Bu | 6-NHCH$_2$Ph-4-OMe | 4-COOMe | $C_{26}H_{31}N_5O_4$ |
| 7 | n-Bu | 6-NHCH$_2$Ph | 4-COOH | $C_{24}H_{27}N_5O_3$ |
| 8 | n-Bu | 6-NH(CH$_2$)$_2$Ph | 4-COOH | $C_{25}H_{29}N_5O_3$ |
| 9 | n-Bu | 6-NH(CH$_2$)$_3$Ph | 4-COOH | $C_{26}H_{31}N_5O_3$ |
| 10 | n-Bu | 6-NHCH$_2$Ph-4-OMe | 4-COOH | $C_{25}H_{29}N_5O_4$ |
| 11 | n-Bu | 6-OCH$_2$Ph | 4-COOH | $C_{24}H_{26}N_4O_4$ |
| 12 | n-Pen | 6-OMe | 4-COOH | $C_{19}H_{24}N_4O_4$ |

TABLE 1-continued

| No. | R¹ | R² | R³ | Molecular formula |
|---|---|---|---|---|
| 13 | n-Hex | 6-OMe | 4-COOH | $C_{20}H_{26}N_4O_4$ |
| 14 | n-Pr | 6-OMe | 4-COOH | $C_{17}H_{20}N_4O_4$ |
| 15 | Et | 6-OMe | 4-COOH | $C_{16}H_{18}N_4O_4$ |
| 16 | n-Bu | 6-NHPh | 4-COOH | $C_{23}H_{25}N_5O_3$ |
| 17 | n-Pen | 6-NH(CH$_2$)$_2$Ph | 4-COOH | $C_{27}H_{33}N_5O_3$ |
| 18 | n-Pen | 6-NH(CH$_2$)$_3$Ph | 4-COOH | $C_{28}H_{35}N_5O_3$ |
| 19 | n-Bu | 6-NH(CH$_2$)$_4$Ph | 4-COOEt | $C_{29}H_{37}N_5O_3$ |
| 20 | n-Bu | 6-OEt | 4-COOH | $C_{19}H_{24}N_4O_4$ |
| 21 | n-Bu | 6-O-n-Bu | 4-COOH | $C_{21}H_{28}N_4O_4$ |
| 22 | n-Pen | 6-OCH$_2$Ph | 4-COOH | $C_{25}H_{28}N_4O_4$ |
| 23 | n-Bu | 6-Cl | 4-COOH | $C_{17}H_{19}N_4O_3Cl$ |
| 24 | n-Bu | 6-Br | 4-COOH | $C_{17}H_{19}N_4O_3Br$ |
| 25 | n-Bu | 6-F | 4-COOH | $C_{17}H_{19}N_4O_3F$ |
| 26 | n-Bu | 6-Ph | 4-COOH | $C_{23}H_{24}N_4O_3$ |
| 27 | n-Bu | 6-(CH$_2$)$_2$Ph | 4-COOH | $C_{25}H_{26}N_4O_3$ |
| 28 | n-Bu | 6-(CH$_2$)$_4$Ph | 4-COOH | $C_{27}H_{30}N_4O_3$ |
| 29 | n-Bu | 6-NH$_2$ | 4-COOH | $C_{17}H_{21}N_5O_3$ |
| 30 | n-Bu | 6-NHMe | 4-COOH | $C_{18}H_{23}N_5O_3$ |

TABLE 2

| No. | R¹ | R² | R³ | Molecular formula |
|---|---|---|---|---|
| 31 | n-Bu | 6-NH-n-Bu | 4-COOH | $C_{21}H_{29}N_5O_3$ |
| 32 | n-Bu | 6-NH-n-Hex | 4-COOH | $C_{23}H_{33}N_5O_3$ |
| 33 | n-Pr | 6-NHCH$_2$Ph-4-OMe | 4-COOH | $C_{24}H_{27}N_5O_4$ |
| 34 | n-Bu | 6-NH(CH$_2$)$_2$Ph-4-OMe | 4-COOH | $C_{26}H_{31}N_5O_4$ |
| 35 | n-Bu | 6-N(n-Pr)CH$_2$Ph | 4-COOH | $C_{27}H_{33}N_5O_3$ |
| 36 | n-Bu | 6-N(n-Bu)(CH$_2$)$_4$Ph | 4-COOH | $C_{31}H_{41}N_5O_3$ |
| 37 | n-Bu | 6-N(n-Bu)Ph | 4-COOH | $C_{27}H_{33}N_5O_3$ |
| 38 | n-Bu | 6-N(n-Hex)Ph | 4-COOH | $C_{29}H_{37}N_5O_3$ |
| 39 | n-Bu | 6-NHC(=O)Me | 4-COOH | $C_{19}H_{23}N_5O_4$ |
| 40 | n-Bu | 6-NHC(=O)Et | 4-COOH | $C_{20}H_{25}N_5O_4$ |
| 41 | n-Bu | 6-NHC(=O)n-Bu | 4-COOH | $C_{22}H_{29}N_5O_4$ |
| 42 | n-Bu | 6-NHC(=O)n-Hex | 4-COOH | $C_{24}H_{33}N_5O_4$ |
| 43 | n-Bu | 6-NHC(=O)(CH$_2$)$_2$Ph | 4-COOH | $C_{26}H_{29}N_5O_4$ |
| 44 | n-Bu | 6-NHC(=O)(CH$_2$)$_4$Ph | 4-COOH | $C_{28}H_{33}N_5O_4$ |
| 45 | n-Bu | 6-NHC(=O)(CH$_2$)$_6$Ph | 4-COOH | $C_{30}H_{37}N_5O_4$ |
| 46 | n-Bu | 6-NHC(=O)CHPh$_2$ | 4-COOH | $C_{31}H_{31}N_5O_4$ |
| 47 | n-Bu | 6-Cl | 4-OH | $C_{16}H_{19}N_4O_2Cl$ |
| 48 | n-Bu | 6-Cl | 4-OMe | $C_{17}H_{22}N_4O_2Cl$ |
| 49 | n-Bu | 6-Cl | 4-O-n-Bu | $C_{20}H_{27}N_4O_2Cl$ |
| 50 | n-Bu | 6-Cl | 4-O-n-Hex | $C_{22}H_{31}N_4O_2Cl$ |
| 51 | n-Bu | 6-Ph | 4-OH | $C_{22}H_{24}N_4O_2$ |
| 52 | n-Bu | 6-CH$_2$Ph | 4-OMe | $C_{24}H_{28}N_4O_2$ |
| 53 | n-Bu | 6-(CH$_2$)$_2$Ph | 4-OMe | $C_{25}H_{30}N_4O_2$ |
| 54 | n-Bu | 6-Ph | 4-NHMe | $C_{23}H_{27}N_5O$ |
| 55 | n-Bu | 6-Ph | 4-N(Me)$_2$ | $C_{24}H_{29}N_5O$ |
| 56 | n-Bu | 6-CH$_2$Ph | 4-N(Me)$_2$ | $C_{25}H_{31}N_5O$ |
| 57 | n-Bu | 6-(CH$_2$)$_2$Ph | 4-N(Me)$_2$ | $C_{26}H_{33}N_5O$ |
| 58 | n-Bu | 6-(CH$_2$)$_4$Ph | 4-N(Me)$_2$ | $C_{28}H_{37}N_5O$ |
| 59 | n-Bu | 6-(CH$_2$)$_3$Ph | 4-N(Et)$_2$ | $C_{29}H_{39}N_5O$ |
| 60 | n-Bu | 6-(CH$_2$)$_6$Ph | 4-N(Et)$_2$ | $C_{32}H_{45}N_5O$ |

TABLE 3

| No. | R¹ | R² | R³ | Molecular formula |
|---|---|---|---|---|
| 61 | n-Bu | 6-N(Me)CH$_2$Ph | 4-COOH | $C_{25}H_{29}N_5O_3$ |
| 62 | n-Bu | 6-NH-n-Bu | 4-COOEt | $C_{23}H_{33}N_5O_3$ |
| 63 | n-Bu | 6-NH-n-Hex | 4-COO-n-Bu | $C_{27}H_{41}N_5O_3$ |
| 64 | H | 6-OMe | 4-COOH | $C_{14}H_{14}N_4O_4$ |
| 65 | H | 6-CH$_2$Ph | 4-COOH | $C_{20}H_{18}N_4O_3$ |
| 66 | H | 6-O(CH$_2$)$_4$Ph | 4-COOH | $C_{23}H_{24}N_4O_4$ |
| 67 | H | 6-NHPh | 4-COOH | $C_{19}H_{23}N_5O_3$ |
| 68 | H | 6-NHCH$_2$Ph | 4-COOH | $C_{20}H_{25}N_5O_3$ |
| 69 | H | 6-Cl | 4-COOH | $C_{13}H_{11}N_4O_3Cl$ |
| 70 | H | 6-CF$_3$ | 4-COOH | $C_{14}H_{11}N_4O_3F_3$ |
| 71 | H | 6-CF$_2$CF$_3$ | 4-COOH | $C_{15}H_{11}N_4O_3F_5$ |
| 72 | H | 6-NH$_2$ | 4-COOH | $C_{13}H_{13}N_5O_3$ |
| 73 | H | 6-NH-n-Bu | 4-COOH | $C_{17}H_{21}N_5O_3$ |
| 74 | H | 6-NHC(=O)Me | 4-COOH | $C_{15}H_{15}N_5O_4$ |
| 75 | H | 6-NHC(=O)n-Bu | 4-COOH | $C_{18}H_{21}N_5O_4$ |
| 76 | H | 6-NHC(=O)n-Pen | 4-COOH | $C_{19}H_{23}N_5O_4$ |
| 77 | NH-n-Pr | 6-NHCH$_2$Ph | 4-COOH | $C_{23}H_{26}N_6O_3$ |
| 78 | NH-n-Pr | 6-Cl | 4-COOH | $C_{16}H_{18}N_5O_3Cl$ |
| 79 | NH-n-Pr | 6-NHC(=O)Me | 4-NH$_2$ | $C_{18}H_{25}N_7O_2$ |
| 80 | NH-n-Pr | 6-CF$_3$ | 4-COOH | $C_{17}H_{18}N_5O_3F_3$ |
| 81 | NH-n-Pr | 6-OMe | 4-COOH | $C_{17}H_{21}N_5O_4$ |
| 82 | NH-n-Pr | 6-OCH$_2$Ph | 4-COOH | $C_{23}H_{25}N_5O_4$ |
| 83 | NH-n-Pr | 6-NH$_2$ | 4-COOH | $C_{16}H_{20}N_6O_3$ |
| 84 | NH-n-Pr | 6-NHCH$_2$Ph-4-OMe | 4-COOH | $C_{24}H_{28}N_6O_4$ |
| 85 | NH-n-Pr | 6-Cl | 4-OH | $C_{15}H_{18}N_5O_2$ |
| 86 | n-Bu | 6-OMe | 4-CN$_4$H | $C_{18}H_{22}N_8O_2$ |
| 87 | n-Bu | 6-OMe | 4-SO$_3$H | $C_{17}H_{22}N_4O_5S$ |
| 88 | n-Bu | 6-NHPh | 4-OMe | $C_{23}H_{27}N_5O_2$ |
| 89 | n-Bu | 6-NHCH$_2$Ph | 4-OMe | $C_{24}H_{29}N_5O_2$ |
| 90 | n-Bu | 6-NH(CH$_2$)$_2$Ph | 4-OMe | $C_{25}H_{31}N_5O_2$ |

TABLE 4

| | | | Elemental analysis | | | | | |
|---|---|---|---|---|---|---|---|---|
| | | | Calculated | | | Found | | |
| No. | Molecular weight | Mass spectrum | C (%) | H (%) | N (%) | C (%) | H (%) | N (%) |
| 1 | 376.84 | 376(EI) | 57.37 | 5.62 | 14.87 | 57.32 | 5.48 | 14.82 |
| 2 | 358.40 | 358(EI) | 60.32 | 6.19 | 15.63 | 60.04 | 6.58 | 15.35 |
| 3 | 447.54 | 447(EI) | 67.09 | 6.53 | 15.65 | 66.83 | 6.93 | 15.39 |
| 4 | 461.57 | 461(EI) | 67.66 | 6.77 | 15.17 | 67.81 | 6.85 | 15.32 |
| 5 | 475.59 | 475(EI) | 68.19 | 6.99 | 14.73 | 68.10 | 7.13 | 14.64 |
| 6 | 477.57 | 477(EI) | 65.39 | 6.54 | 14.66 | 65.01 | 6.64 | 14.28 |
| 7 | 433.51 | 433(EI) | 66.50 | 6.28 | 16.15 | 66.13 | 6.54 | 15.78 |
| 8 | 447.54 | 447(EI) | 67.09 | 6.53 | 15.65 | 67.05 | 6.38 | 15.61 |
| 9 | 461.57 | 461(EI) | 67.66 | 6.77 | 15.17 | 67.67 | 6.84 | 15.18 |
| 10 | 463.54 | 463(EI) | 64.78 | 6.31 | 15.11 | 65.02 | 6.26 | 15.35 |
| 11 | 434.50 | 434(EI) | 66.34 | 6.03 | 12.89 | 65.98 | 5.61 | 12.53 |
| 12 | 372.43 | 372(EI) | 61.28 | 6.50 | 15.04 | 60.93 | 6.68 | 14.69 |
| 13 | 386.45 | 386(EI) | 62.16 | 6.78 | 14.50 | 62.34 | 6.61 | 14.68 |
| 14 | 344.37 | 344(EI) | 59.29 | 5.85 | 16.27 | 59.48 | 5.78 | 16.46 |
| 15 | 330.34 | 330(EI) | 58.17 | 5.49 | 16.96 | 58.29 | 5.55 | 17.08 |
| 16 | 419.49 | 419(EI) | 65.86 | 6.01 | 16.70 | 65.70 | 5.82 | 16.54 |
| 17 | 475.59 | 475(EI) | 68.19 | 6.99 | 14.73 | 68.28 | 7.14 | 14.82 |
| 18 | 489.62 | 489(EI) | 68.69 | 7.21 | 14.30 | 68.98 | 6.90 | 14.59 |
| 19 | 503.65 | 503(EI) | 69.16 | 7.41 | 13.91 | 68.92 | 7.44 | 13.67 |
| 20 | 372.43 | 372(EI) | 61.28 | 6.50 | 15.04 | 61.38 | 6.62 | 15.14 |
| 21 | 400.48 | 400(EI) | 62.98 | 7.05 | 13.99 | 62.97 | 7.13 | 13.98 |
| 22 | 448.52 | 448(EI) | 66.95 | 6.29 | 12.49 | 66.80 | 5.89 | 12.34 |
| 23 | 362.82 | 362(EI) | 56.28 | 5.28 | 15.44 | 56.06 | 5.49 | 15.22 |
| 24 | 407.27 | 406(EI) | 50.14 | 4.70 | 13.76 | 50.32 | 4.54 | 13.94 |
| 25 | 346.36 | 346(EI) | 58.95 | 5.53 | 16.18 | 58.81 | 5.52 | 16.04 |
| 26 | 404.47 | 404(EI) | 68.30 | 5.98 | 13.85 | 68.46 | 5.87 | 14.01 |
| 27 | 430.51 | 430(EI) | 69.75 | 6.09 | 13.01 | 70.08 | 5.82 | 13.34 |
| 28 | 458.56 | 458(EI) | 70.72 | 6.59 | 12.22 | 70.84 | 6.80 | 12.34 |
| 29 | 343.39 | 343(EI) | 59.46 | 6.16 | 20.39 | 59.35 | 6.15 | 20.28 |
| 30 | 357.41 | 357(EI) | 60.49 | 6.49 | 19.59 | 60.68 | 6.57 | 19.78 |

TABLE 5

| | | | Elemental analysis | | | | | |
|---|---|---|---|---|---|---|---|---|
| | | | Calculated | | | Found | | |
| No. | Molecular weight | Mass spectrum | C (%) | H (%) | N (%) | C (%) | H (%) | N (%) |
| 31 | 399.50 | 399(EI) | 63.14 | 7.32 | 17.53 | 62.98 | 7.41 | 17.37 |
| 32 | 427.55 | 427(EI) | 64.61 | 7.78 | 16.38 | 64.72 | 7.61 | 16.49 |
| 33 | 449.51 | 449(EI) | 64.13 | 6.05 | 15.58 | 63.77 | 5.84 | 15.22 |
| 34 | 477.57 | 477(EI) | 65.39 | 6.54 | 14.66 | 65.35 | 6.58 | 14.62 |

TABLE 5-continued

| | | | Elemental analysis | | | | | |
|---|---|---|---|---|---|---|---|---|
| | | | Calculated | | | Found | | |
| No. | Molecular weight | Mass spectrum | C (%) | H (%) | N (%) | C (%) | H (%) | N (%) |
| 35 | 475.59 | 475(EI) | 68.19 | 6.99 | 14.73 | 67.92 | 7.10 | 14.46 |
| 36 | 531.70 | 531(EI) | 70.03 | 7.77 | 13.17 | 69.89 | 7.03 | 13.04 |
| 37 | 475.59 | 475(EI) | 68.19 | 6.99 | 14.73 | 67.94 | 7.05 | 14.48 |
| 38 | 503.65 | 503(EI) | 69.16 | 7.41 | 13.91 | 69.07 | 7.25 | 13.82 |
| 39 | 385.42 | 385(EI) | 59.21 | 6.02 | 18.17 | 59.11 | 6.18 | 18.07 |
| 40 | 399.45 | 399(EI) | 60.14 | 6.31 | 17.53 | 60.31 | 6.57 | 17.70 |
| 41 | 427.51 | 427(EI) | 61.81 | 6.84 | 16.38 | 61.76 | 6.62 | 16.33 |
| 42 | 455.56 | 455(EI) | 63.28 | 7.30 | 15.37 | 63.55 | 6.99 | 15.64 |
| 43 | 475.55 | 475(EI) | 65.67 | 6.15 | 14.73 | 65.42 | 6.31 | 14.48 |
| 44 | 503.60 | 503(EI) | 66.78 | 6.61 | 13.91 | 66.71 | 6.50 | 13.84 |
| 45 | 531.66 | 531(EI) | 67.77 | 7.02 | 13.17 | 67.54 | 7.05 | 12.94 |
| 46 | 537.62 | 537(EI) | 69.26 | 5.81 | 13.03 | 69.31 | 5.89 | 13.08 |
| 47 | 334.81 | 334(EI) | 57.40 | 5.72 | 16.73 | 57.72 | 5.76 | 17.05 |
| 48 | 349.84 | 349(EI) | 58.37 | 6.34 | 16.01 | 58.43 | 6.33 | 16.07 |
| 49 | 390.92 | 390(EI) | 61.45 | 6.96 | 14.33 | 61.28 | 6.99 | 14.16 |
| 50 | 418.97 | 418(EI) | 63.07 | 7.46 | 13.37 | 62.95 | 7.70 | 13.25 |
| 51 | 376.46 | 376(EI) | 70.19 | 6.43 | 14.88 | 70.45 | 6.23 | 15.14 |
| 52 | 404.51 | 404(EI) | 71.26 | 6.98 | 13.85 | 70.99 | 6.66 | 13.58 |
| 53 | 418.54 | 418(EI) | 71.74 | 7.23 | 13.39 | 71.94 | 7.11 | 13.59 |
| 54 | 389.50 | 389(EI) | 70.92 | 6.99 | 17.98 | 70.85 | 6.94 | 17.91 |
| 55 | 403.53 | 403(EI) | 71.44 | 7.24 | 17.36 | 71.09 | 7.34 | 17.01 |
| 56 | 417.56 | 417(EI) | 71.91 | 7.48 | 16.77 | 72.23 | 7.83 | 17.09 |
| 57 | 431.58 | 431(EI) | 72.36 | 7.71 | 16.23 | 72.24 | 7.94 | 16.11 |
| 58 | 459.64 | 459(EI) | 73.17 | 8.11 | 15.24 | 73.10 | 8.05 | 15.17 |
| 59 | 473.66 | 473(EI) | 73.54 | 8.30 | 14.79 | 73.36 | 8.35 | 14.61 |
| 60 | 515.75 | 515(EI) | 74.52 | 8.80 | 13.58 | 74.91 | 8.69 | 13.97 |

TABLE 6

| | | | Elemental analysis | | | | | |
|---|---|---|---|---|---|---|---|---|
| | | | Calculated | | | Found | | |
| No. | Molecular weight | Mass spectrum | C (%) | H (%) | N (%) | C (%) | H (%) | N (%) |
| 61 | 447.54 | 447(EI) | 67.09 | 6.53 | 15.65 | 66.88 | 6.76 | 15.44 |
| 62 | 427.55 | 427(EI) | 64.61 | 7.78 | 16.38 | 64.68 | 7.71 | 16.45 |
| 63 | 483.66 | 483(EI) | 67.05 | 8.54 | 14.48 | 67.19 | 8.38 | 14.62 |
| 64 | 302.29 | 302(EI) | 55.63 | 4.67 | 18.53 | 55.66 | 4.89 | 18.56 |
| 65 | 362.39 | 362(EI) | 66.29 | 5.01 | 15.46 | 66.43 | 4.63 | 15.60 |
| 66 | 420.47 | 420(EI) | 65.70 | 5.75 | 13.32 | 65.69 | 5.75 | 13.31 |
| 67 | 369.43 | 369(EI) | 61.77 | 6.28 | 18.96 | 61.60 | 6.28 | 18.79 |
| 68 | 383.45 | 383(EI) | 62.65 | 6.57 | 18.26 | 62.35 | 6.46 | 17.96 |
| 69 | 306.71 | 306(EI) | 50.91 | 3.62 | 18.27 | 50.80 | 3.84 | 18.16 |
| 70 | 340.26 | 340(EI) | 49.42 | 3.26 | 16.47 | 49.02 | 3.10 | 16.58 |
| 71 | 390.27 | 390(EI) | 46.16 | 2.84 | 14.36 | 45.97 | 3.20 | 14.17 |
| 72 | 287.28 | 287(EI) | 54.35 | 4.56 | 24.38 | 54.30 | 4.72 | 24.33 |
| 73 | 343.39 | 343(EI) | 59.46 | 6.16 | 20.39 | 59.44 | 6.32 | 20.37 |
| 74 | 329.32 | 329(EI) | 54.71 | 4.59 | 21.27 | 54.74 | 4.23 | 21.30 |
| 75 | 371.40 | 371(EI) | 58.21 | 5.70 | 18.86 | 58.00 | 5.74 | 18.65 |
| 76 | 385.42 | 385(EI) | 59.21 | 6.02 | 18.17 | 59.12 | 6.07 | 18.08 |
| 77 | 434.50 | 434(EI) | 63.58 | 6.03 | 19.34 | 63.64 | 6.33 | 19.40 |
| 78 | 408.26 | 407(EI) | 47.07 | 4.44 | 17.15 | 47.04 | 4.30 | 17.12 |
| 79 | 371.44 | 371(EI) | 58.20 | 6.78 | 26.40 | 58.14 | 6.85 | 26.34 |
| 80 | 397.36 | 397(EI) | 51.39 | 4.57 | 17.62 | 51.07 | 4.96 | 17.30 |
| 81 | 359.39 | 359(EI) | 56.82 | 5.89 | 19.49 | 57.21 | 6.14 | 19.88 |
| 82 | 435.48 | 435(EI) | 63.44 | 5.79 | 16.08 | 63.40 | 5.90 | 16.04 |
| 83 | 344.37 | 344(EI) | 55.80 | 5.85 | 24.40 | 55.59 | 6.19 | 24.19 |
| 84 | 464.53 | 464(EI) | 62.06 | 6.08 | 18.09 | 61.95 | 5.87 | 17.98 |
| 85 | 300.34 | 300(EI) | 59.99 | 6.04 | 23.32 | 59.99 | 6.06 | 23.32 |
| 86 | 382.43 | 382(FAB) | 56.53 | 5.80 | 29.30 | 56.69 | 5.97 | 29.46 |
| 87 | 394.45 | 394(FAB) | 51.77 | 5.62 | 14.20 | 51.50 | 6.02 | 13.93 |
| 88 | 405.50 | 405(EI) | 68.13 | 6.71 | 17.27 | 68.02 | 6.83 | 16.98 |
| 89 | 419.53 | 419(EI) | 68.71 | 6.97 | 16.69 | 68.55 | 7.01 | 16.55 |
| 90 | 433.55 | 433(EI) | 69.26 | 7.21 | 16.15 | 69.38 | 7.02 | 16.27 |

The compounds of the present invention may be prepared by a process known per se. For example, The compounds of the present invention may be prepared through the scheme (1) comprising the steps (a) to (c) as follows: Scheme (1):

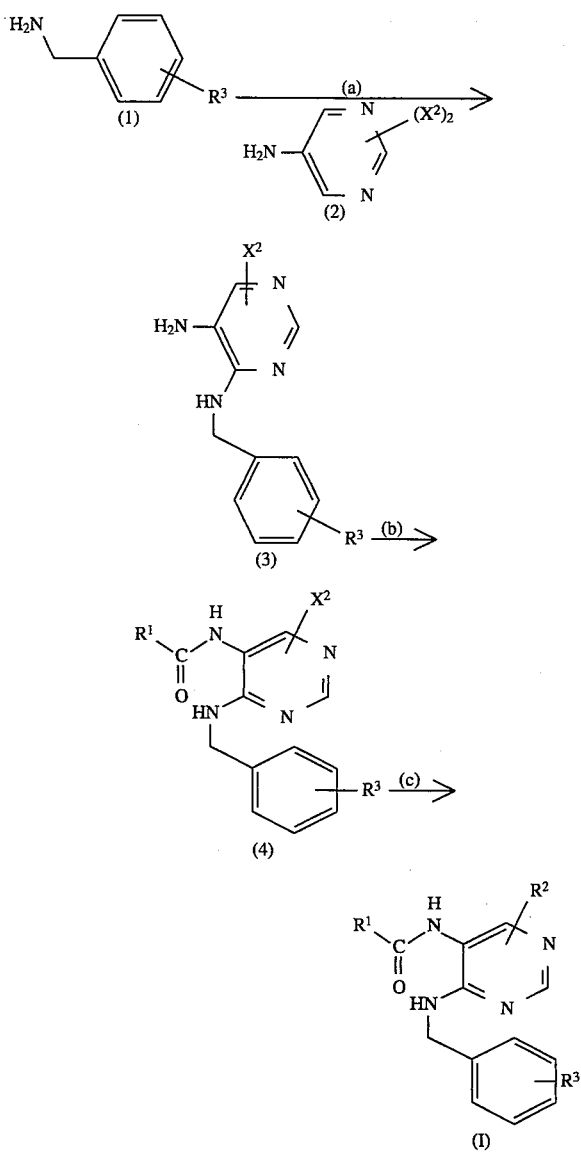

Step (a):

The compound of the formula (1) is protected, if necessary, and then, reacted with the compound of the formula (2) wherein $X^2$ is a halogen atom to obtain the compound of the formula (3). The reaction is carried out in an organic solvent, such as ethanol, butanol, dioxane, dimethylsulfoxide, N,N-dimethylformamide, or N,N-diethylformamide, in the presence of a base, such as triethylamine, pyridine, picoline or lutidine, at 20° to 150° C., preferably under reflux, for 5 to 72 hours while stirring.

Step (b)

The compound of the formula (3) is dissolved in a solvent, such as N,N-dimethylformamide, dichloromethane, tetrahydrofuran, acetone, chloroform or pyridine, and the compound which can convert the amino group to R1—CONH group wherein $R^1$ has the same meaning as above is added thereto. The reaction is carried out at 0° to 100° C. for 3 to 40 hours to obtain the compound of the formula (4). The compound which can convert the amino group to R1—CONH group is, for example, valeric chloride, when $R^1$ is n-butyl. When $R^1$ is other group, such a compound may be appropriately selected by those skilled in the art in view of the desired $R^1$.

Step (c)

The compound of the formula (4) is reacted with the compound which can convert the $X^2$ group to the $R^2$ group wherein $R^2$ has the same meaning as above to obtain the compound of the formula (I). The reaction with the amine is carried out in an organic solvent, such as butanol, ethanol, dioxane, dimethylsulfoxide or N,N-dimethylformamide, at 20° to 150° C., preferably under reflux, for 3 to 72 hours while stirring. The reaction with the alcohol is carried out in alcohol in the presence of alkaline aqueous solution, at 20° to 150° C. for 3 to 72 hours, after adding a solvent, such as tetrahydrofuran or dioxane, if necessary. The compound which can convert the $X^2$ group to the $R^2$ group is, for example, benzylamine when $R^2$ is benzylamino group. When $R^2$ is other group, such a compound may be appropriately selected by those skilled in the art in view of the desired $R^2$.

The ester compound of the formula (I) can be hydrolyzed in an organic solvent, such as methanol, ethanol or butanol in the presence of alkaline aqueous solution at 20° to 100° C. for 1 to 48 hours while stirring and deposited with acid, and then converted to the free compound of the formula (I).

Further, the salt, particularly the pharmaceutically acceptable salt, of the compound of the formula (I) can be prepared by utilizing the compound of the formula (I) and an equivalent amount of an alkali, evaporating the solvent or concentrating the solution, and drying and purifying the residue.

The pyrimidine derivative of the formula (I) according to the present invention or the pharmaceutically acceptable salt thereof is sufficiently effective in improvement of the renal dysfunction without any function to blood pressure. Therefore, the present invention relates to a pharmaceutical composition, particularly an anti-kidney disease agent, containing the pyrimidine derivative of the formula (I) or the pharmaceutically acceptable salt thereof as an active ingredient.

The compound of the formula (I) is effective as an agent for treating a kidney disease, such as nephritis, nephropathy, renal failure, nephrotic syndrome, asymptomatic proteinuria, hematuria, diabetic nephropathy, kidney disease induced by medicine, urinary tract infectious disease, or prostatitis. The compound of the formula (I) according to the present invention may be administered orally or parenterally (such as percutaneously, intravenously or intraperitoneally).

The compound of the formula (I) according to the present invention was orally administered to mice at the dose of 500 mg/kg, but no death was observed during one week.

The compound of the formula (I) may be formulated by adding one or more pharmaceutically acceptable additives, to powder, tablet, granule, capsule, suppository, injection, or oral solution. As the additives, there may be mentioned, for example, magnesium stearate, talc, lactose, dextrin, starches, methylcellulose, fatty acid glycerides, water, propyleneglycol, macrogols, alcohols, crystalline celluloses, hydroxypropylcellulose, low substituted hydroxypropylcellulose, carmelloses, povidone, polyvinylalcohol, or calcium stearate. Further, coloring agent, stabilizer, antioxidant, preservative, pH adjusting agent, isotonicity, solubilizing agent and/or soothing agent may be contained, if necessary. The granule, tablet, or capsule may be coated with a coating base, such as hydroxypropylmethyl cellulose or hydroxypropylmethyl cellulose phthalate.

The compound of the formula (I) may be contained at an amount of 0.1 to 500 mg, preferably 1 to 100 mg in a dose unit. The dose of the compound of the formula (I) is 0.1 to 150 mg/kg body weight, preferably 1 to 100 mg/kg body weight. The dose may be administered once a day, or divided twice or 3 times a day. The dose may be appropriately selected with respect to symptom of the patient.

The inventors of the present invention analyzed the three-dimensional structure of angiotensin II in solution by means of a method as originally developed, and studied the properties of various compounds, taking into account the affinities to angiotensin II in solution. More particularly, antagonism to angiotensin II receptor subtype 1 which is known to participates in antihypertensive function, a function to improve renal dysfunction in a renal dysfunction model animal, a function against blood pressure or the like were investigated in detail. As a result, the inventors found the compound of the formula (I) or a salt thereof has desired properties which are completely different from those of conventionally known antihypertensive compounds.

As mentioned above, the compound of the formula (I) or a salt thereof exhibits antagonism to the angiotensin II receptor subtype 1 which is one-hundredth ($1/100$) to one-thousandth ($1/1000$) or less as large as that of the conventionally known antagonist having a standard activity as an antihypertensive agent. The compound of the formula (I) or a salt thereof exhibits a function to improve renal dysfunction without substantial antagonism. In view of the conventional knowledge, it is greatly surprising that there exist compounds having such properties. It is still unclear how the compound of the formula (I) exhibits such properties. It is assumed that the properties are brought about from, for example, the specific antagonism to a angiotensin II receptor (i.e., a new receptor other than the known subtypes 1 and 2) which participates in renal interstitial cell growth causing exacerbation of renal failure, or accumulation of the compound to kidney, although the present invention is not limited to said assumption. Further, there is a possibility of a mechanism completely different from that of antagonism to angiotensin II receptor.

Even if the compound of the formula (I) according to the present invention or a salt thereof is classified in an angiotensin II receptor antagonist, it has the properties essentially different from those of the known angiotensin II receptor antagonists which have been developed as an antihypertensive agent, i.e., the antagonists having a strong antagonism to the receptor and a function to lower blood pressure. If the compound of the formula (I) or a salt thereof is not classified in an angiotensin II receptor antagonist, it is apparently different therefrom. Accordingly, the compound of the formula (I) according to the present invention or a salt thereof is novel with respect to the chemical structure, functional effects, and medical utility.

As above, the compound of the formula (I) according to the present invention or a salt thereof is sufficiently effective to renal dysfunction without affecting blood pressure. Therefore, it is possible to appropriately treat kidney diseases without any such problem as acute renal failure with the drugs having such properties while controlling blood pressure at a desired level by means of a suitable antihypertensive drug if necessary.

EXAMPLES

The present invention now will be further illustrated by, but is by no means limited to, the following Examples.

Example 1

Preparation of methyl 4-[[(6-chloro-5-amino) pyrimidin-4-yl]aminomethyl]benzoate (3-1): Step (a)

Hydrogen chloride gas was blown into methanol (250 ml) on ice with stirring to prepare a methanol solution of hydrogen chloride (44.4 g). To the solution, 4-aminomethylbenzoic acid (25.70 g) was added at room temperature and the mixture was heated under reflux with stirring for 28 hours to obtain an almost homogeneous solution. The solvent was evaporated under reduced pressure from the solution to obtain methyl 4-aminomethylbenzoate hydrochloride (33.11 g) as a colorless solid.

A light yellow suspension of the resulting compound (21.53 g), 5-amino-4,6-dichloro-pyrimidine (15.93 g), 1-butanol (260 ml), and triethylamine (41 ml) was dissolved by heating to the reflux temperature and was stirred under reflux for 19 hours. The solvent was evaporated under reduced pressure, and water (250 ml) and chloroform (500 ml) were added to the residue, and the whole was shaken. The precipitated light yellow solid was filtered out to obtain the crude product (17.20 g) of the above-captioned compound. The crude product was recrystallized from ethyl acetate/chloroform (1:1) to obtain the above-captioned compound (14.85 g) as colorless crystals.

Melting Point: 197.5°–198.5° C.

$^1$H-NMR (500 MHz, CDCl$_3$) δ: 3.84(s,3H), 4.71(d,2H), 5.09(s,2H), 7.44–7.46(m, 1H), 7.44(d,2H), 7.71(s,1H), 7.92(d,2H)

Example 2

Preparation of methyl 4-[[(6-chloro-5-valeramido) pyrimidin-4-yl]aminomethyl]benzoate (4-1) (compound No. 1): Step (b)

A suspension of the compound (3-1) (14.63 g) prepared in Example 1 in dry N,N-dimethyl formamide (70 ml) was sealed. Valeryl chloride (7.24 g) was added by a syringe with stirring at room temperature to obtain a homogeneous light yellow solution. After the solution was heated on a water bath at 80° C., triethylamine (10 ml) and dry N,N-dimethylformamide (140 ml) were added by a syringe and the mixture was stirred for 5.5 hours. The solvent was evaporated under reduced pressure. Water (150 ml) was added to the residue, and was extracted with chloroform (400 ml). The organic layer was dried over anhydrous magnesium sulfate, and concentrated to obtain a yellow viscous product (31.66 g). The product was recrystallized from ethyl acetate/hexane to obtain the above-captioned compound (10.18 g) as colorless scaly crystals.

Melting Point: 166.0°–168.0° C.

$^1$H-NMR (500 MHz, CDCl$_3$) δ: 0.95(t,3H), 1.41(sext, 2H), 1.73(quint, 2H), 2.48(t,2H), 3.90(s,3H), 4.77(d,2H), 6.15(dd,1H), 7.08(s,1H), 7.39(d,2H), 8.00(d,2H), 8.28 (s,1H)

Example 3

Preparation of 4-[[(6-methoxy-5-valeramido) pyrimidin-4-yl]aminomethyl]benzoic acid (compound No. 2)

To a solution of the compound (4-1) (6.00 g) prepared in Example 2 in methanol (90 ml), 1N NaOH (30 ml) was added, and the solution was allowed to stand at room temperature for 26.5 hours. The reaction solution was concentrated to dryness. To the residue, 1N HCl aqueous solution (31 ml) was added to adjust pH to 7. A precipitated viscous product was dissolved in chloroform, and washed with water and saturated brine. The organic layer was dried over anhydrous sodium sulfate, and concentrated to obtain crude yellow oil (6.90 g). The crude oil was purified by silica gel column chromatography (Kieselgel 60=300 g, chloroform/methanol=30/) to obtain the above-captioned compound (2.27 g) as a light yellow solid.

$^1$H-NMR (500 MHz, CDCl$_3$) δ: 0.88(t,3H), 1.37(sext, 2H), 1.78(quint,2H), 2.76(t,2H), 4.20(s,3H), 5.50(s,2H), 7.20(d,2H), 8.04(d,2H), 8.53(s,1H)

Example 4

Preparation of methyl 4-[[(6-benzylamino-5-valeramido) pyrimidin-4-yl]aminomethyl]benzoate (Compound No. 3): Step (c)

A suspension of the compound (4-1) (0.50 g) prepared in above-mentioned Example 2, 1-butanol (7 ml), and benzylamine (0.57 g) was heated under reflux with stirring to obtain a homogeneous light yellow solution. The solution was heated under reflux with stirring for 23 hours. The solvent was evaporated under reduced pressure on a water bath at 80° C. Water (15 ml) was added to the residue, and a mixture was extracted with chloroform (40 ml in total).

The organic layer was dried over anhydrous magnesium sulfate, and concentrated to obtain light yellow oil (0.76 g). The crude oil was purified by silica gel column chromatography (Kieselgel 60=70 g, chloroform/ethyl acetate=1/1) to obtain the above-captioned compound (0.28 g) as colorless crystals.

Melting Point: 144.0°–148.0° C.

$^1$H-NMR (500 MHz, CDCl$_3$) δ: 0.81(t,1.5H), 0.86(t, 1.5H), 1.19(sext,1H), 1.31(sext,1H), 1.47(quint,1H), 1.65(quint,1H), 2.04(t,1H), 2.37(t,1H), 3.90(s,3H), 4.60–4.73(m,4H), 4.82(dd,0.5H), 4.95(dd,0.5H), 5.09(dd, 0.5H), 5.20(dd,0.5H), 6.04(s,0.5H), 6.33(s,0.5H), 7.21–7.39(m,7H), 7.98(d,2H), 8.22(s,0.5H), 8.25(s,0.5H)

Example 5

Preparation of methyl 4-[[(6-phenethylamino-5-valeramido)pyrimidin-4-yl]aminomethyl]benzoate (Compound No. 4): Step (c)

The procedure described in Example 4 was repeated, except that the compound (4-1) (0.50 g) prepared in Example 2 was reacted with phenethylamine(0.49 g) to obtain the above-captioned compound (0.24 g) as colorless crystals.

Melting Point: 130.0°–133.0° C.

$^1$H-NMR (500 MHz, CDCl$_3$) δ: 0.82(t,1.5H), 0.90(t, 1.5H), 1.17(sext,1H), 1.32(sext,1H), 1.43(quint,1H), 1.52–1.63(m,1H), 1.85–1.98(m,1H), 2.30(t,1H), 2.86–2.90(m,2H), 3.65–3.77(m,2H), 3.90(s,3H), 4.50(dd, 0.5H), 4.66–4.77(m,2H), 4.80(dd,0.5H), 4.93(dd,0.5H), 5.16(dd,0.5H), 5.94(s,0.5H), 6.17(s,0.5H),7.18–7.37(m, 7H), 7.97(d,2H), 8.21(s,0.5H), 8.23(s,0.5H)

Example 6

Preparation of methyl 4-[[(6-phenylpropylamino-5-valeramido)pyrimidin-4-yl]aminomethyl]benzoate (Compound No. 5): Step (c)

The procedure described in Example 4 was repeated, except that the compound (4-1) (0.50 g) prepared in Example 2 was reacted with phenylpropylamine (0.50 g), and the crude product was recrystallized from ethyl acetate/hexane (1:1) to obtain the above-captioned compound (0.21 g) as colorless crystals.

Melting Point: 146.0°–149.0° C.

$^1$H-NMR (500 MHz, CDCl$_3$) δ: 0.82(t,1.5H), 0.93 (t, 1.5H), 1.21(sext,1H), 1.37(sext,1H), 1.50(quint,1H), 1.68(quint,1H), 1.89–1.98(m,2H), 2.03(t,1H), 2.36(t,1H), 2.67–2.73(m,2H), 3.46–3.53(m,2H), 3.90(s,3H), 4.40(dd, 0.5H), 4.67–4.73(m,2H), 4.75(dd,0.5H), 4.88(dd,0.5H), 5.17(dd,0.5H), 5.95(s,0.5H), 6.08(s,0.5H), 7.11–7.37(m, 7H), 7.98(d,2H), 8.19(s,0.5H), 8.21(s,0.5H)

Example 7

Preparation of methyl 4-[[[6-(4-methoxybenzyl) amino-5-valeramido]pyrimidin-4-yl]aminomethyl]benzoate (Compound No. 6): Step (c)

The procedure described in Example 4 was repeated, except that the compound (4-1) (0.38 g) prepared in Example 2 was reacted with 4-methoxybenzylamine (0.56 g) to obtain the above-captioned compound (0.10 g) as colorless crystals.

Melting Point: 173.0°–176.0° C.
$^1$H-NMR (500 MHz, $CDCl_3$) δ: 0.81(t,1.5H), 0.86(t, 1.5H), 1.18(sext,1H), 1.30(sext,1H), 1.46(quint,1H), 1.65(quint, 1H), 2.02(t,1H), 2.36(t,1H), 3.79(s,3H), 3.90(s, 3H), 4.53–4.63(m,2H), 4.68–4.77(m,2.5H), 4.94(dd,0.5H), 5.01(dd,0.5H), 5.18(dd,0.5H), 6.00(s,0.5H), 6.31(s,0.5H), 6.85–6.88(m,2H), 7.21–7.26(m,2H), 7.34–7.39(m.2H), 7.98(d,2H), 8.22(s,0.5H), 8.25(s,0.5H)

Example 8

Preparation of 4-[[(6-benzylamino-5-valeramido) pyrimidin-4-yl]aminomethyl]benzoic acid (Compound No. 7)

The Compound No. 3 (0.20 g) prepared in Example 4 was dissolved in methanol (30 ml), and 1N NaOH (4.5 ml) and water (10 ml) were added. The solution was stirred at room temperature for 24 hours. The solvent was evaporated under reduced pressure on a water bath at 40° C. The residue was redissolved in water (20 ml), and acidified with 1N HCl aqueous solution (7.5 ml in total) to obtain a precipitate. The precipitated solid was filtered to obtain a colorless solid (0.20 g). The solid was recrystallized from water/ethanol (5/2) to obtain the above-captioned compound (0.15 g) as colorless granulated crystals.

Melting Point: 213.0°–233.5° C. (decomposed)
$^1$H-NMR (500 MHz, $d_6$-DMSO) δ: 0.90(t,3H), 1.33(sext, 2H), 1.59(quint,2H), 2.42(t,2H), 4.59(d,2H), 4.65(d,2H), 7.22–7.33(m,7H), 7.40(d,2H), 7.87(d.2H), 8.05(s,1H), 8.82(s,1H), 12.84(bs,1H)

The reaction solution was concentrated without acidification, and the residue was purified to obtain a sodium salt of the above-captioned compound. Example 9
Preparation of 4-[[(6-phenethylamino-5-valeramido) pyrimidin-4-yl]aminomethyl]benzoic acid (Compound No. 8)

The procedure described in Example 8 was repeated, except that the Compound No. 4 (0.20 g) prepared in Example 5 was used to obtain a precipitated solid (0.17 g) after acidification. The solid was recrystallized from water/ethanol (5/4) to obtain the above-captioned compound (0.075 g) as colorless granulated crystals.

Melting Point: 215.0°–216.0° C. (decomposed)
$^1$H-NMR (500 MHz, $d_6$-DMSO) δ: 0.90(t,3H), 1.32(sext, 2H), 1.57(quint,2H), 2.35(t,2H), 2.77(t,2H), 3.50(q,2H), 4.58(d,2H), 5.91(t,1H), 6.59(t,1H), 7.18–7.30(m,5H), 7.38(d,2H), 7.84(d,2H), 7.91(s,1H), 8.52(s,1H), 12.75(bs, 1H)

Example 10

Preparation of 4-[[(6-phenylpropylamino-5-valeramido) pyrimidin-4-yl]aminomethyl]benzoic acid (Compound No. 9)

The procedure described in Example 8 was repeated, except that the Compound No. 5 (0.24 g) prepared in Example 6 was used to obtain a precipitated solid (0.12 g) after acidification. The solid was recrystallized from water/ethanol (1/1) to obtain the above-captioned compound (0.083 g) as colorless crystals.

Melting Point: 185.0°–190.0° C. (decomposed)
$^1$H-NMR (500 MHz, $d_6$-DMSO) δ: 0.90(t,3H), 1.33(sext, 2H), 1.59(quint,2H), 2.38(t,2H), 2.60(t,2H), 2.54–2.65(m, 2H), 4.59(d,2H), 5.46(s,1H), 7.15–7.29(m,6H), 7.38(d,2H), 7.85(d,2H), 7.93(s,1H), 8.57(s,1H), 12.79(bs,1H)

Example 11

Preparation of 4-[[[6-(4-methoxybenzyl amino-5-valeramido]pyrimidin-4-yl]aminomethyl]benzoic acid (Compound No. 10)

The procedure described in Example 8 was repeated, except that the Compound No. 6 (0.092 g) prepared in Example 7 was used to obtain a precipitated solid (0.055 g) after acidification. The solid was recrystallized from water/ethanol (1/1) to obtain the above-captioned compound (0.014 g) as colorless crystals.

Melting Point: 216.0°–218.0° C. (decomposed)
$^1$H-NMR (500 MHz, $d_6$-DMSO) δ: 0.88(t,3H), 1.31(sext, 2H), 1.58(quint,2H), 2.37(t,2H), 3.71(s,3H), 4.45(d,2H), 4.58(d,2H), 6.39(t,1H), 6.60(t,1H), 6.83(d,2H), 7.21(d,2H), 7.38(d,2H), 7.83–7.88(m,3H), 8.56(s,1H), 12.77(bs,1H)
Example 12
Preparation of 4-[[(6-benzyoloxy-5-valermido) pyrimidin-4-yl]aminomethyl]benzoic acid (Compound No. 11)

The compound (4-1) (0.20 g) prepared in Example 2 was dissolve in benzyl alcohol (3 ml). To the solution, 1N NaOH aqueous solution (2.2 ml) was added to obtain an emulsion, and further tetrahydrofuran (20 ml) was added to obtain a homogeneous solution. The solution was stirred at room temperature for 17 hours, and the solvent was evaporated under reduced pressure on a water bath at 40° C. To the residue, 1N HCl aqueous solution (2.2 ml) was added and pH was adjusted to 1. Water (10 ml) was further added, and the reaction solution was extracted with chloroform (10 ml). The organic layer was concentrated to obtain oil. Water (300 ml) was added to the oil, and a precipitated solid was filtered out to obtain a colorless solid (0.17 g; melting point= 185.5°–215.0° C.). Methanol (50 ml) was added to the solid to obtain a homogeneous solution, and further 1N NaOH aqueous solution (5 ml) and water (10 ml) were added. The solution was stirred at room temperature for 18 hours, and the solvent was evaporated under reduced pressure on a water bath at 40° C. The residue was redissolved in water (10 ml), and adjusted with 1N HCl aqueous solution (7 ml) to pH 1. A precipitated solid (0.15 g) was filtered, and the solid was recrystallized from water/methanol (3/10) to obtain the above-captioned Compound No. 11 (0.054 g) as colorless needle crystals.

Melting Point: 195.5°–197.0° C. (decomposed)
$^1$H-NMR(500 MHz, $d_6$-DMSO) δ: 0.81(t,3H), 1.29(sext, 2H), 1.62(quint,2H), 2.78(t,2H), 5.57(s,2H), 5.62(s,2H), 5.63(s,1H), 7.24(d,2H), 7.36–7.54(m,6H), 7.89(d,2H), 8.51(s,1H), 12.94(bs,1H)

Example 13

Preparation of 4-[[(6-chloro-5-amino)pyrimidin-4-yl]aminomethyl]anisole (3-48): step (a)
A mixture of 5-amino-4,6-dichloro-pyrimidine (5.00 g), 4aminomethylanisole (4.12 g) , 1-butanol (100 ml), and dry triethylamine (4.9 ml) was heated to the reflux temperature, and stirred for 48 hours to obtain a homogeneous light orange solution. The solvent was evaporated under reduced pressure to obtain yellowish brown oil (13.7 g). Water (100 ml) was added to the oil, and a precipitated solid was filtered out to obtain a crude light yellow product (7.42 g). The filtrate was extracted with ethyl acetate (100 ml), and dried over anhydrous magnesium sulfate. The solvent was evaporated under reduced pressure to obtain a light yellow solid (0.59 g). The solid and the above crude product were combined, and recrystallized from ethyl acetate to obtain the above-captioned compound (5.08 g) as colorless crystals.

Melting Point: 186.0°–188.0° C.

$^1$H-NMR (500 MHz, CDCl$_3$) δ: 3.34(bs,2H), 3.81(s,3H), 4.61(d,2H), 5.01(bs,1H), 6.88(d,2H), 7.28(d,2H), 8.12(s, 1H)

Example 14

Preparation of 4-[[(6-Chloro-5-Valeramido) pyrimidin-4-yl] aminomethyl]anisole (4-48) (Compound No. 48): Step (b)

Dry N,N-dimethylformamide (200 ml) was added to the compound (3-48) (25.32 g) prepared in Example 13, and sealed to obtain a homogeneous colorless solution. Valeryl chloride (10.34 g) was added by a syringe under stirring at room temperature over five minutes. The mixture was heated to 80° C. over 15 minutes, and dry triethylamine (17 ml) was added. The mixture was stirred for 6 hours and allowed to stand overnight. The solvent was evaporated under reduced pressure. The residue was dissolved in chloroform (250 ml), washed with water, dried over anhydrous magnesium sulfate, and concentrated to obtain a yellow solid (45.06 g). The solid was purified by silica gel column chromatography (Kieselgel 60=250 g, ethyl acetate/n-hexane=2/3) to obtain the above-captioned compound (17.55 g) as colorless needle crystals.

Melting Point: 135.0°–138.0° C.

$^1$H-NMR (500 MHz, CDCl$_3$) δ: 0.93(t,3H), 1.39(sext, 2H), 1.70(quint,2H), 2.43(t,2H), 3.79(s,3H), 4.63(d,2H), 5.88(bs,1H), 6.87(d,2H), 6.98(bs,1H), 7.26(d,2H), 8.30(s, 1H)

Example 15

Preparation of 4-[[(6-benzylamino-5-valeramido) pyrimidin-4-yl]aminomethyl]anisole (Compound No. 89): Step (c)

The procedure described in Example 4 was repeated, except that the compound (4-48) (1.05 g) prepared in Example 14 was reacted with benzylamine (0.64 g), and the reaction product was purified by silica gel column chromatography (Kieselgel 60=60 g, ethyl acetate/chloroform=1/1) to obtain the above-captioned compound (0.72 g) as colorless crystals.

Melting Point: 158.0°–159.0° C.

$^1$H-NMR (500 MHz, CDCl$_3$) δ: 0.79–0.85(m,3H), 1.17(sext,1H), 1.28(sext,1H), 1.44(quint, 1H), 1.58–1.64(m, 2H), 2.01(t,1H), 2.32(t,1H), 3.79(s,3H), 4.52–4.65(m,4H), 4.68(t,0.5H), 4.76(t,0.5H), 4.83(t,0.5H), 5.02(t,0.5H), 6.00(s,0.5H), 6.30(s,0.5H), 6.81–6.86(m,2H), 7.21–7.35(m, 7H), 8.24(s,0.5H), 8.26(s,0.5H)

Example 16

Preparation of 4-[[(6-phenethylamino-5-valeramido) pyrimidin-4-yl]aminomethyl]anisole (compound No. 90): Step (c)

The procedure described in Example 4 was repeated, except that the compound (4-48) (1.05 g) prepared in Example 14 was reacted with phenethylamine (0.73 g), and the reaction product was purified by silica gel column chromatography (Kieselgel 60= 70 g, ethyl acetate/chloroform =1/1) to obtain the above-captioned compound (0.86 g) as colorless crystals.

Melting Point: 151.0°–152.5° C.

$^1$H-NMR (500 MHz, CDCl$_3$) δ: 0.82(t,1.5H), 0.89(t, 1.5H), 1.17(sext,1H), 1.30(sext,1H), 1.42(quint, 1H), 1.58(quint,1H), 1.61(s,1H), 1.84–1.95(m,1H), 2.26(t,1H), 2.87–2.91(m,2H), 3.68–3.77(m,2H), 3.78(s,3H), 4.48–4.62(m,2.5H), 4.72(t,0.5H), 4.76(t,0.5H), 4.94(t, 0.5H), 5.88(s,0.5H), 6.10(s,0.5H), 6.83–6.86(m,2H), 7.17–7.32(m,7H), 8.24(s,0.5H), 8.25(s,0.5H)

Example 17

Preparation of methyl 4-[[(6-N-benzylmethylamino-5-valeramido) pyrimidin-4-yl]aminomethyl]benzoate: Step (c)

The procedure described in Example 4 was repeated, except that the Compound No. 1 (0.50 g) prepared in Example 2 was reacted with 1-butanol (7 ml) and N-benzylmethylamine (0.49 g), and the reaction product was purified by silica gel column chromatography (Kieselgel 60=70 g, ethyl acetate/chloroform=3/1) to obtain the above-captioned compound (0.21 g) as colorless crystals.

$^1$H-NMR (500 MHz, CDCl$_3$) δ: 0.78(t,3H), 1.14(sext, 2H), 1.38(quint,2H), 1.77(t,2H), 3.00(s,3H), 3.89(s,3H), 4.46(s,2H), 4.73(d,2H), 5.59(t,1H), 6.52(s,1H), 7.27–7.41(m,7H), 7.97(d,2H), 8.23(s,1H)

Example 18

Preparation of 4-[[(6-N-benzylmethylamino-5-valeramido) pyrimidin-4-yl]aminomethyl]benzoic acid (Compound No. 61)

The compound (0.19 g) prepared in Example 17 was dissolved in methanol (30 ml). Water (10 ml) and 1N NaOH aqueous solution (4.1 ml) were added to the solution. The reaction solution was stirred at room temperature for 22 hours and the solvent was evaporated under reduced pressure at 40° C. The residue was redissolve in water (10 ml), and 1N HCl aqueous solution was added until a white turbidity appeared. The reaction mixture was extracted with chloroform (40 ml), dried over anhydrous magnesium sulfate, and concentrated to obtain a colorless solid (0.14 g). The solid was recrystallized from water/methanol (1/1) to obtain the above-captioned compound (0.087 g) as colorless granulated crystals.

Melting Point: 160.0°–170.0° C.

$^1$H-NMR (500 MHz, CDCl$_3$) δ: 0.82(t,3H), 1.22(sext, 2H), 1.44(quint,2H), 2.20(t,2H), 2.91(s,3H), 4.61(d,2H), 4.68(s,2H), 5.49(s,1H), 6.85(t,1H), 7.21–7.34(m,5H), 7.38(d,2H), 7.85(d,2H), 7.90(s,1H), 8.81(s,1H)

Example 19

Acute toxicity

Five-week-old ICR female mice (5 mice per group) were bred for acclimation for a week. Then, the compounds of the present invention were dissolved or dispersed in an aqueous solution of 0.5% methylcellulose, and orally administered to the mice in a single dosage (500 mg/kg). The number of deaths was observed for 6 days after the administration. The results are shown in Table 7.

TABLE 7

| Compound No. | Number of deaths/number of survivals |
| --- | --- |
| 1 | 0/5 |
| 2 | 0/5 |
| 7 | 0/5 |
| 8 | 0/5 |
| 9 | 0/5 |
| 10 | 0/5 |
| 11 | 0/5 |
| 48 | 0/5 |
| 61 | 0/5 |
| 89 | 0/5 |
| 90 | 0/5 |

Example 20

Binding to receptors

In this Example, the affinity to the angiotensin II receptor subtype 1 or subtype 2 was evaluated by a binding assay in accordance with the method described in Biochem. Pharmacol., 33, 4057–4062 (1984).

Specifically, the measurement of the total binding in the presence of each drug was performed as follows:

A mixture (final volume=0.25 ml) of a drug in a given concentration (the drug was dissolved in DMSO, and diluted to a double volume with a buffer attached to a drug discovery system to prepare sample for the assay; 0,025 ml), a tracer (0.025 ml), and receptors (0.2 ml) was incubated [in the case of the angiotensin II receptor subtype 1 ($AT_1$), at room temperature for 3 hours, and in the case of the subtype 2 ($AT_2$), at 37° C. for 1 hour]. Then, the reaction mixture was filtered with suction (GF/C filter was used in $AT_1$, and GF/B filter was used in $AT_2$). The filter papers after filtration with suction (the tracer bound to the receptors) were counted by a γ-well counter (ARC-500, Aloka). The non-specific bindings were measured by repeating the above method, except that a large excess amount of a displacer was added. The specific binding of the drug in the given concentration was calculated by subtracting the non-specific binding from the total binding, respectively.

In $AT_1$ and $AT_2$, the percentages to inhibit the bindings of radioactive ligands (tracer) to receptors by the drugs to be tested ($IC_{50}$ value of concentration to show 50% inhibition, or binding inhibition % in 100 μM) were measured, using the drugs to be tested and control drugs in the given concentration. The results are shown in Table 8.

TABLE 8

| Compound No. | $IC_{50}$ $AT_1$ (nM) | Binding inhibition % in 100 μM | |
|---|---|---|---|
| | | $AT_1$ | $AT_2$ |
| 1 | | 11 | 0 |
| 2 | 28000 | | 0 |
| 7 | | 1 | 0 |
| 8 | | 0 | 0 |
| 9 | | 6 | 0 |
| 10 | | 6 | 0 |
| 11 | 15000 | | 0 |
| 48 | | 0 | 0 |
| 61 | | 42 | 0 |
| 89 | | 11 | 0 |
| 90 | | 20 | 0 |
| DuP753 | 20 | | 0 |

In $AT_1$,
receptor: from adrenal glands in rabbits
tracer: $^3$H-angiotensin II
control drug: DuP753
(displacer): DuP753
In $AT_2$,
receptor: from cerebellar cortex in bovine
tracer: $^{125}$I-Tyr$^4$-angiotensin II
control drug: angiotensin II (human)
(displacer): angiotensin II (human)

As clear from Table 8, $IC_{50}$ values of the compounds of the present invention to the angiotensin II subtype 1 receptor were not less than 15000 nM, whereas $IC_{50}$ value of DuP753 used as a control substance was 20 nM. Therefore, it can be said that the compounds of the present invention having $IC_{50}$ values of not less than 15000 nM exhibit no inhibitory effect on the subtype 1 receptor. The fact that the compounds of the present invention exhibit no binding activity to the subtype 1 receptor shows that such compounds are completely different from conventional ACE inhibitors or angiotensin II antagonists in action mechanism.

Example 21

Action to depress blood pressure

The compounds of the present invention and the reference substance were forcedly administered per os to kidney disease model rats, and the action to depress blood pressure was observed. The kidney disease model rats were prepared by ligature of branches of renal artery in accordance with the conventional method, that is, the left hilum renalis of Sprague-Dawley female rats was exposed under anesthesia, and one of four secondary branches of renal artery was left unligated, while the remaining three branches were ligated, respectively. After a week, the hilum renalis (artery, vein, and ureter) of the right kidney were further ligated to thereby prepare the rats whose renal function was lowered to approximately ⅛ of the normal function. Each group consisted of eight rats. The drugs to be tested (20 mg/kg) were administered to each administering group, and only water was administered to control group. After two days from the administration, the systolic blood pressure was measured by the tail cuff method using a blood pressure measuring apparatus (UR5000; Ueda). The average of the blood pressures is shown in Table 9.

TABLE 9

| Compound No. | Blood pressure (mmHg) |
|---|---|
| 1 | 210 |
| 2 | 201 |
| 7 | 208 |
| 8 | 203 |
| 9 | 204 |
| 10 | 208 |
| 11 | 202 |
| 48 | 207 |
| 61 | 205 |
| 89 | 204 |
| 90 | 208 |
| control | 210 |
| DuP753 | 130 |

In comparison with the control group, the reference substance (DuP753) clearly showed the action to depress the blood pressure. On the contrary, influence on the blood pressure was not substantially shown in the compounds of this invention.

Example 22

Renal function indicatory value (action to kidney diseases)

The kidney disease model rats were prepared as in Example 21. Fifteen groups (8 rats per group) were sleeked in a manner so that there were no major differences between each group in the serum creatinine value and the urea nitrogen value indicating renal function. The rats in each group were allowed to freely take up feed and water. To the rats in the administering group, the compounds of this invention or the reference substance (DuP753) were forcedly administered per os at the dose of 20 mg/kg/day every day. To the rats in the control group, only water was forcedly administered per os every day. After two weeks, 0.2 ml of blood was collected from the carotid artery of the rat under anesthesia, and centrifuged to obtain serum. Using 25 μl of the serum, serum creatinine (Scr) was measured by a creatinine analytical instrument (Beckman). Using 10 μl of the serum, urea nitrogen (BUN) was measured by a BUN analytical instrument (Beckman). Creatinine clearance was evaluated as follows:

After serum creatinine measurement, rats were placed in urinary metabolic cages for 24 hours to collect urine. Urinary creatine concentration (Ucr) was measured by a creatinine analytical instrument, and total volume of urination (Uvol) was also measured. Creatinine clearance (CCr) was calculated by the following formula:

$$CCr(ml/min) = \frac{Ucr(mg/dl) \times Uvol(ml)}{Scr(mg/dl) \times 24 \times 60(min)}$$

TABLE 10

| Compound No. | Creatinine mg/dl | Urea nitrogen mg/dl | Creatinine clearance ml/min |
|---|---|---|---|
| 1 | 1.7 | 84 | 0.29 |
| 2 | 1.6 | 78 | 0.35 |
| 7 | 1.6 | 80 | 0.33 |
| 8 | 1.6 | 79 | 0.33 |
| 9 | 1.6 | 80 | 0.31 |
| 10 | 1.6 | 81 | 0.33 |
| 11 | 1.6 | 78 | 0.35 |
| 48 | 1.7 | 83 | 0.30 |
| 61 | 1.6 | 81 | 0.32 |
| 89 | 1.6 | 80 | 0.33 |
| 90 | 1.7 | 82 | 0.29 |
| control | 2.0 | 100 | 0.20 |
| DuP753 | 1.6 | 80 | 0.32 |

When the compounds of the present invention were administered, the serum creatinine value and the urea nitrogen value which increase with aggravation of renal failure clearly became lower values and creatinine clearance indicating renal function was clearly improved in comparison with the control substance. The pharmacological effects were comparable to those of the reference substance, and it was shown that the compounds of the present invention do not substantially exhibit conventional angiotensin II receptor antagonism and blood pressure depression action, but improve kidney diseases.

Example 23

Action to survival time of kidney diseased animals

The kidney disease model rats were prepared as in Example 21. Fifteen groups (8 rats per group) were prepared in a manner so that there was no major difference between the groups in the serum creatinine value and the urea nitrogen value indicating renal function. The rats in each group were allowed to freely take up feed and water. To the rats in the administering group, the compounds of the present invention or the reference substance (DuP753) were forcedly administered per os at the dose of 20 mg/kg/day every day. To the rats in the control group, only water was forcedly administered per os every day. If kidney diseases are aggravated, the rat will die of uremia. Thus, the survival time was observed as comprehensive indication of the improvement effect on the kidney diseases. The results are shown in Table 11. The observation period was eight weeks. Thus if all rats survived, the average survival time is eight weeks and it is an upper limit.

TABLE 11

| Compound No. | Average survival time (weeks) |
|---|---|
| 1 | 6.9 |
| 2 | 7.5 |
| 7 | 7.0 |
| 8 | 7.1 |
| 9 | 6.9 |
| 10 | 7.0 |
| 11 | 7.5 |
| 48 | 6.9 |
| 61 | 6.9 |
| 89 | 7.0 |
| 90 | 6.9 |

TABLE 11-continued

| Compound No. | Average survival time (weeks) |
|---|---|
| control | 5.0 |
| DuP753 | 6.9 |

The compounds of the present invention clearly prolonged the survival time of the kidney disease model rats. The effect was comparable or superior to that of the reference substance. It was shown that the compounds of this invention do not substantially exhibit known angiotensin II receptor antagonism and blood pressure depression action, but prolonged the survival time of the rats which died of kidney diseases.

Example 24

The compound No. 1 (10 mg), lactose (36 mg), corn starch (150 mg), microcrystalline cellulose (29 mg), and magnesium stearate (5 mg) were mixed, and tableted to prepare tablets (230 mg/tablet).

Although the present invention has been described with reference to specific embodiments, various changes and modifications obvious to those skilled in the art are deemed to be within the spirit, scope, and concept of the invention.

We claim:

1. A pyrimidine derivative or a salt thereof of formula (I):

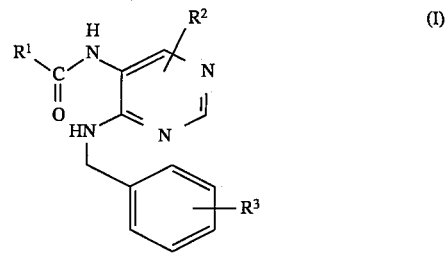

wherein $R^1$ is a hydrogen atom, an alkyl group of 1 to 6 carbon atoms, a haloalkyl group of 1 to 6 carbon atoms, or a —$NHR^{11}$ group;

$R^2$ is a hydrogen or a halogen atom, an alkyl group of 1 to 6 carbon atoms, a haloalkyl group of 1 to 6 carbon atoms, —$(CH_2)_m C_6H_5$, —$NH_2$, —$NHR^{12}$, —$NH(CH_2)_n C_6H_5$, —$NH(CH_2)_p C_6H_4$—$OR^{13}$, —$N(R^{14})(CH_2)_q C_6H_5$, —$NHC(=O)R^{15}$, —$NHC(=O)(CH_2)_r C_6H_5$, —$NHCC(=O)CH(C_6H_5)_2$, —$OR^{16}$, or —$O(CH_2)_s C_6H_5$ group;

$R^3$ is —COOH, —$COOR^{17}$, hydroxyl, —$OR^{18}$, —$NH_2$, —$N(R^{19})_2$, —$NHR^{20}$, a 5-membered cyclic group containing 2 to 4 heteroatoms, wherein said heteroatoms are selected from the group consisting of a nitrogen atom, an oxygen atom, and a sulfur atom, or a sulfonic acid group;

$R^{11}$ is an alkyl group of 1 to 6 carbon atoms or a haloalkyl group of 1 to 6 carbon atoms;

$R^{12}$, $R^{13}$, $R^{14}$, $R^{15}$, $R^{16}$, $R^{17}$, $R^{18}$, $R^{19}$, and $R^{20}$ are independently an alkyl group of 1 to 6 carbon atoms;

m is 0 or an integer of 1 to 6;

n is 0 or an integer of 1 to 6;

p is 0 or an integer of 1 to 6;

q is 0 or an integer of 1 to 6;

r is 0 or an integer of 1 to 6; and s is 0 or an integer of 1 to 6.

2. The pyrimidine derivative or a salt thereof according to claim 1, wherein $R^1$ is a hydrogen atom, an alkyl group of 1 to 5 carbon atoms, a haloalkyl group of 1 to 5 carbon atoms, or a —$NHR^{11}$ group;

$R^2$ is a hydrogen or a halogen atom, an alkyl group of 1 to 4 carbon atoms, a haloalkyl group of 1 to 4 carbon atoms, —$(CH_2)_mC_6H_5$, —$NH_2$, —$NHR^{12}$, —$NH(CH_2)_nC_6H_5$, —$NH(CH_2)_pC_6H_4$—$OR^{13}$, —$N(R^{14})(CH_2)_qC_6H_5$, —$NH(=O)R^{15}$, —$NHC(=O)(CH_2)_rC_6H_5$, —$NHC(=O)CH(C_6H_5)_2$, —$OR^{16}$, or —$O(CH_2)_sC_6H_5$ group;

$R^3$ is —COOH, —$COOR^{17}$, hydroxyl, —$OR^{18}$, —$NH_2$, —$N(R^{19})_2$, —$NHR^{20}$, a 5-membered cyclic group containing 2 to 4 heteroatoms, wherein said heteroatoms are selected from the group consisting of nitrogen atom, an oxygen atom, and a sulfur atom, or a sulfonic acid group;

$R^{11}$ is an alkyl group of 1 to 5 carbon atoms or a haloalkyl group of 1 to 5 carbon atoms;

$R^{12}$, $R^{13}$, $R^{14}$, $R^{15}$, $R^{16}$, $R^{17}$, $R^{18}$, $R^{19}$, and $R^{20}$ are independently an alkyl group of 1 to 4 carbon atoms;

m is 0 or an integer of 1 to 4;

n is 0 or an integer of 1 to 4;

p is 0 or an integer of 1 to 4;

q is 0 or an integer of 1 to 4;

r 1s 0 or an integer of 1 to 4; and s is 0 or an integer of 1 to 4.

3. The pyrimidine derivative or a salt thereof according to claim 1, wherein $R^2$ is at the 2- or 6-position of the pyrimidine ring, and $R^3$ is at the 4-position of the phenyl ring.

4. The pyrimidine derivative or a salt thereof according to claim 1, wherein $R^2$ is at the 6-position of the pyrimidine ring, and $R^3$ is at the 4-position of the phenyl ring.

5. A pharmaceutical composition comprising a pyrimidine derivative or a salt thereof of formula (I):

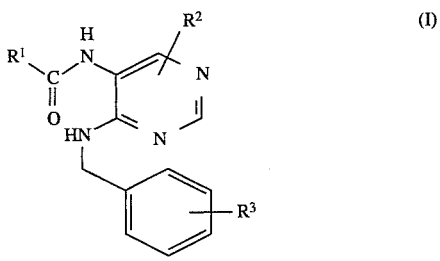

(I)

wherein $R^1$ is a hydrogen atom, an alkyl group of 1 to 6 carbon atoms, a haloalkyl group of 1 to 6 carbon atoms, or —$NHR^{11}$ group;

$R^2$ is a hydrogen or a halogen atom, an alkyl group of 1 to 6 carbon atoms, a haloalkyl group of 1 to 6 carbon atoms, —$(CH_2)_mC_6H_5$, —$NH_2$, —$NHR^{12}$, —$NH(CH_2)_nC_6H_5$, —$NH(CH_2)_pC_6H_4$—$OR^{13}$, —$N(R^{14})(CH_2)_qC_6H_5$, —$NHC(=O)R^{15}$, —$NHC(=O)(CH_2)_rC_6H_5$, —$NHC(=O)CH(C_6H_5)_2$, —$OR^{16}$, or —$O(CH_2)_sC_6H_5$ group;

$R^3$ is —COOH, —$COOR^{17}$, hydroxyl, —$OR^{18}$, —$NH_2$, —$N(R^{19})_2$, —$NHR^{20}$, a 5-membered cyclic group containing 2 to 4 heteroatoms, wherein said heteroatoms are selected from the group consisting of a nitrogen atom, an oxygen atom, and a sulfur atom, or a sulfonic acid group;

$R^{11}$ is an alkyl group of 1 to 6 carbon atoms or a haloalkyl group of 1 to 6 carbon atoms;

$R^{12}$, $R^{13}$, $R^{14}$, $R^{15}$, $R^{16}$, $R^{17}$, $R^{18}$, $R^{19}$, and $R^{20}$ are independently an alkyl group of 1 to 6 carbon atoms;

m is 0 or an integer of 1 to 6;

n is 0 or an integer of 1 to 6;

p is 0 or an integer of 1 to 6;

q is 0 or an integer of 1 to 6;

r is 0 or an integer of 1 to 6; and s is 0 or an integer of 1 to 6, and a pharmaceutically acceptable carrier.

6. A method for treating renal dysfunction while maintaining appropriate blood pressure in a mammal comprising the step of administering to a mammal in need of such treating, a pharmaceutically effective amount of a pyrimidine derivative of formula (I) or a salt thereof:

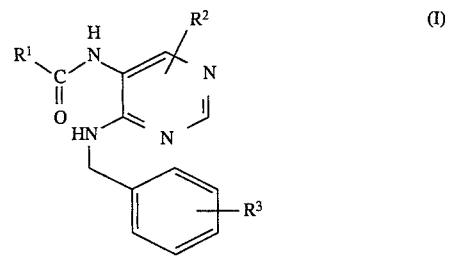

(I)

wherein $R^1$ is a hydrogen atom, an alkyl group of 1 to 6 carbon atoms, a haloalkyl group of 1 to 6 carbon atoms, or a —$NHR^{11}$ group;

$R^2$ is a hydrogen or a halogen atom, an alkyl group of 1 to 6 carbon atoms, a haloalkyl group of 1 to 6 carbon atoms, —$(CH_2)_mC_6H_5$, —$NH_2$, —$NHR^{12}$, —$NH(CH_2)_nC_6H_5$, —$NH(CH_2)_pC_6H_4$—$OR^{13}$, —$N(R^{14})(CH_2)_qC_6H_5$, —$NHC(=O)R^{15}$, —$NHC(=O)CH(C_6H_5)_2$, —$OR^{16}$, or a $2)_pC_6H_4$—$OR^{13}$, —$N(R^{14})$ $(CH_2)_qC_6H_5$, —$NHC(=O)R^{15}$, —$NCH(=O)CH(C_6H_5)_2$, —$OR^{16}$, or a —$O(CH_2)_sC_6H_5$ group;

$R^3$ is —COOH, —$COOR^{17}$, hydroxyl, —$OR^{18}$, —$NH_2$, —$N(R^{19})_2$, —$NHR^{20}$, a 5-membered cyclic group containing 2 to 4 heteroatoms, wherein said heteroatoms are selected from the group consisting of a nitrogen atom, an oxygen atom, and a sulfur atom, or a sulfonic acid group;

$R^{11}$ is an alkyl group of 1 to 6 carbon atoms or a haloalkyl group of 1 to 6 carbon atoms;

$R^{12}$, $R^{13}$, $R^{14}$, $R^{15}$, $R^{16}$, $R^{17}$, $R^{18}$, $R^{19}$, and $R^{20}$ are independently an alkyl group of 1 to 6 carbon atoms;

m is 0 or an integer of 1 to 6;

n is 0 or an integer of 1 to 6;

p is 0 or an integer of 1 to 6;

q is 0 or an integer of 1 to 6;

r is 0 or an integer of 1 to 6; and s is 0 or an integer of 1 to 6.

7. The method according to claim 6, wherein the pyrimidine derivative of formula (I) is effective at treating a renal dysfunction selected from the group consisting of nephritis, nephropathy, renal failure, nephrotic syndrome, asymptomatic proteinuria, hematuria, diabetic nephropathy, kidney disease induced by medicine, urinary tract infection disease, and prostatitis.

* * * * *

UNITED STATES PATENT AND TRADEMARK OFFICE
CERTIFICATE OF CORRECTION

PATENT NO. : 5,585,381
DATED : December 17, 1996
INVENTOR(S) : Mikiro Yanaka, et al.

Page 1 of 2

It is certified that error appears in the above-identified patent and that said Letters Patent is hereby corrected as shown below:

Column 13, lines 43-44, change

"of the above-captioned compound. Example 9
Preparation of 4-[[(6-phenethylamino-5-valeramido) pyri-" to -- of the above-captioned compound.

Example 9

Preparation of 4-[[(6-phenethylamino-5-valeramido) pyri- --.

Column 14, lines 21-23, change

"7.38(d,2H), 7.83-7.88(m,3H), 8.56(s,1H), 12.77(bs,1H)
Example 12
Preparation of 4-[[(6-phenethylamino-5-valeramido) pyrimidin-" to -- 7.38(d,2H), 7.83-7.88(m,3H), 8.56(s,1H), 12.77(bs,1H)

Example 12

Preparation of 4-[[(6-phenethylamino-5-valeramido) pyrimidin- --.

Column 20, (Claim 1), line 49, change "-NHCC(=O)CH($C_6H_5$)$_2$," to

-- -NHC(=O)CH($C_6H_5$)$_2$, --.

Column 21, (Claim 2), line 3, change "claim" to -- Claim --;

(Claim 2), line 18, change "nitrogen" to -- a nitrogen --; and (Claim 2), line 30, change "1s" to -- is --.

UNITED STATES PATENT AND TRADEMARK OFFICE
CERTIFICATE OF CORRECTION

PATENT NO. : 5,585,381
DATED : December 17, 1996
INVENTOR(S) : Mikiro Yanaka, et al.

It is certified that error appears in the above-identified patent and that said Letters Patent is hereby corrected as shown below:

Column 21, (Claim 3), line 33, change "claim" to -- Claim --;

(Claim 4), line 37, change "claim" to -- Claim --.

Column 22, (Claim 6), line 36, delete "2),C₆H₄-"; and (Claim 6), lines 37-39, delete in their entirety.

Signed and Sealed this

Twelfth Day of August, 1997

*Attest:*

BRUCE LEHMAN

*Attesting Officer*  *Commissioner of Patents and Trademarks*